United States Patent
Morigi et al.

[11] Patent Number: 5,976,113
[45] Date of Patent: Nov. 2, 1999

[54] ORIENTED BULK PACKAGE FOR SYRINGES

[75] Inventors: Adriano Morigi, Rutherford; Peter Heyman, Berkeley Heights, both of N.J.

[73] Assignee: Becton Dickison and Company, Franklin Lakes, N.J.

[21] Appl. No.: 09/112,912

[22] Filed: Jul. 9, 1998

[51] Int. Cl.[6] .................................................. A61M 5/00
[52] U.S. Cl. ............................................ 604/199; 206/366
[58] Field of Search .................................... 604/199, 187; 206/366, 365, 364, 363

[56] References Cited

U.S. PATENT DOCUMENTS

| | | | |
|---|---|---|---|
| 4,260,077 | 4/1981 | Schroeder | 206/366 |
| 4,758,230 | 7/1988 | Rycroft | 206/366 X |
| 5,817,065 | 10/1998 | Dufresne et al. | 604/199 |

*Primary Examiner*—John D. Yasko
*Attorney, Agent, or Firm*—Allen W. Wark

[57] ABSTRACT

An assembly (20) of syringes (22) includes a first layer (32) enclosing the syringes. The first layer maintains the syringes in an orientation where some of the syringes have a first, larger end aligned with the second, smaller end of the remainder of the syringes. The first layer also protects the syringes from outside contaminants. A second layer (34) encloses the first layer and protects it from outside contaminants. The syringes and the first layer preferably are sterilized within the second layer 34.

16 Claims, 2 Drawing Sheets

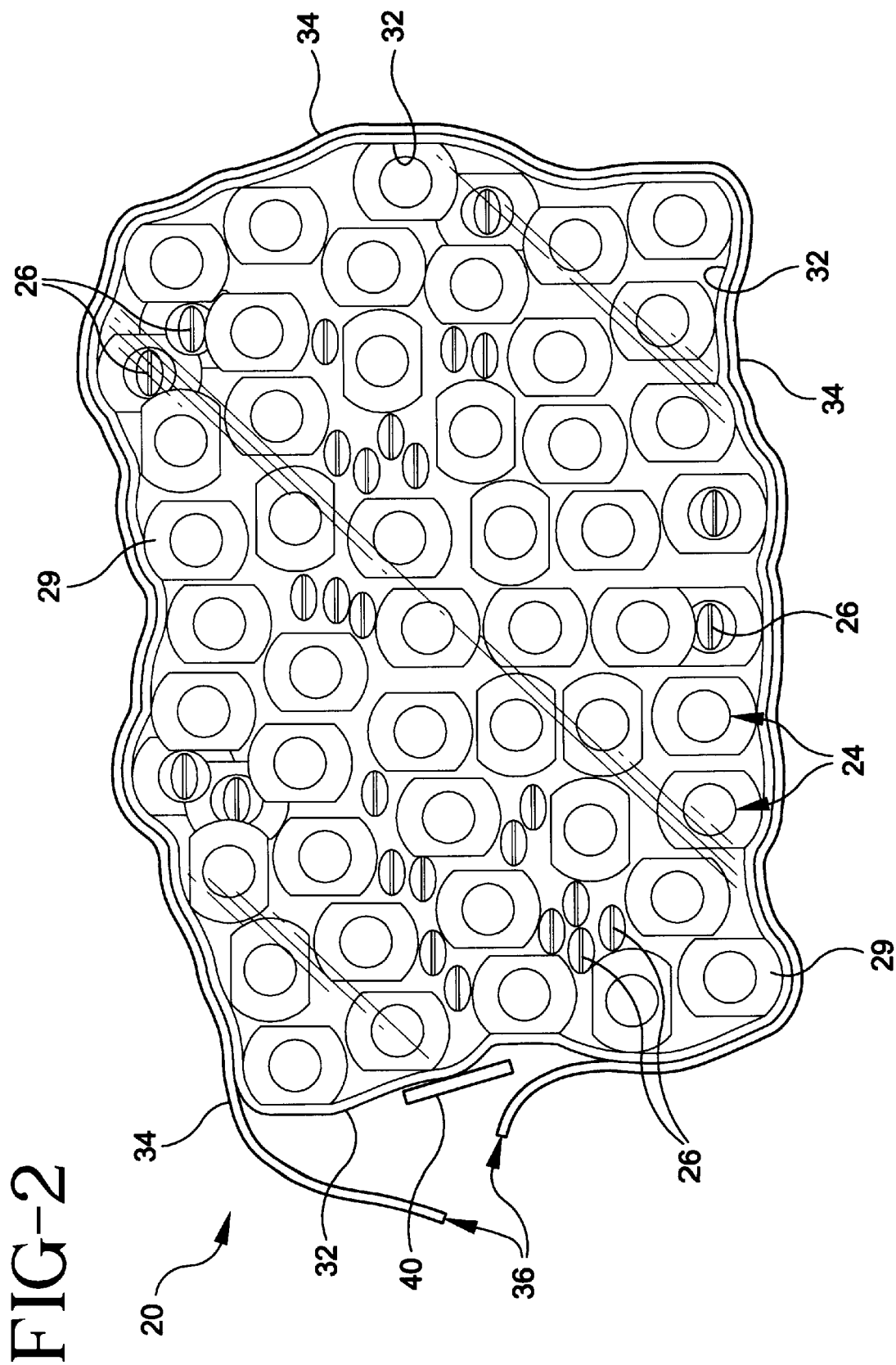

ORIENTED BULK PACKAGE FOR SYRINGES

BACKGROUND OF THE INVENTION

This invention generally relates to an assembly and method for packaging syringes for sterilizing, shipping and later handling them.

Typical syringes utilized for administering injections to patients include a syringe barrel for holding the medicament. Syringe barrels typically are manufactured by companies separate from the pharmaceutical companies. More recently, pharmaceutical companies are increasingly providing pre-filled syringe barrels containing a specific medicament. Syringe manufacturers provide syringe barrels to pharmaceutical companies in a variety of manners.

A typical way of shipping empty syringe barrels to a pharmaceutical company includes utilizing a matrix grid having a plurality of openings for receiving syringe barrels. The matrix grid typically is made of a plastic material and is received within a tub or container. The tub or container is then closed and the contents (i.e., the syringe barrels) are sterilized and ready for shipping to the pharmaceutical company.

While the conventional packaging has proven useful, those skilled in the art are always striving to make improvements. For example, it would be useful to have a packaging arrangement that utilizes less material and reduces the amount of bulk associated with packaging the syringe barrels. The conventional matrix grids suffer from the drawback of providing limited variability in the type of syringe barrels that can be accommodated. Further, the conventional matrix grids only allow a specific number of syringes per package, which tends to increase the number of packages required when a large number of syringe barrels are needed.

U.S. Pat. No. 4,758,230 suggests one alternative to the matrix grids by providing web portions between a plurality of syringe barrels so that the syringe barrels are aligned in a single strip. That patent also suggests placing a plurality of strips side by side and then using a plastic shrink wrap material to hold the syringe barrels together. That arrangement, however, is of limited application because is requires the specific syringe barrels as disclosed in that patent. Further, the web portions between the syringe barrels may not be desired under all circumstances. Lastly, that arrangement still requires a conventional tub or container to maintain the syringes in a sterile package.

Therefore, there is a need for an improved assembly and method for packaging syringe barrels to be shipped to a pharmaceutical company for further handling and later distribution to medical professionals. This invention addresses that need by providing a packaging assembly and method that greatly reduces the costs and amount of material required to place syringe barrels in a sterile package for shipping to pharmaceutical companies and later distribution to medical professionals.

SUMMARY OF THE INVENTION

In general terms, this invention is an assembly of syringes in a specific orientation packaged in a sterile manner. The assembly of this invention includes a plurality of syringe barrels having first and second ends. Each first end has a first outside dimension and each second end has a second outside dimension that is smaller than the first outside dimension. The syringe barrels are aligned with generally parallel axes. The syringe barrels are oriented so that some of the syringe barrels have their first ends adjacent the second ends of the remainder of the syringe barrels. A first layer encloses the plurality of syringes in a sealing manner to thereby protect the syringes from outside contaminants and maintain them in the just-described alignment. A second layer encloses the first layer in a sealing manner to thereby protect the first layer from outside contaminants.

Another feature of this invention is to include a protective piece of relatively stiff material between the first and second layers to protect the first layer from damage while allowing the second layer to be cut open and removed from the package. In the preferred embodiment the first and second layers are made from a shrink wrap plastic material.

The various features and advantages of this invention will become apparent to those skilled in the art from the following detailed description of the currently preferred embodiment. The drawings that accompany the detailed description can be briefly described as follows.

BRIEF DESCRIPTION OF THE DRAWINGS

FIG. 2 is a top elevational view of an assembly of syringes designed according to this invention.

DETAILED DESCRIPTION OF THE PREFERRED EMBODIMENT

Figure 1:
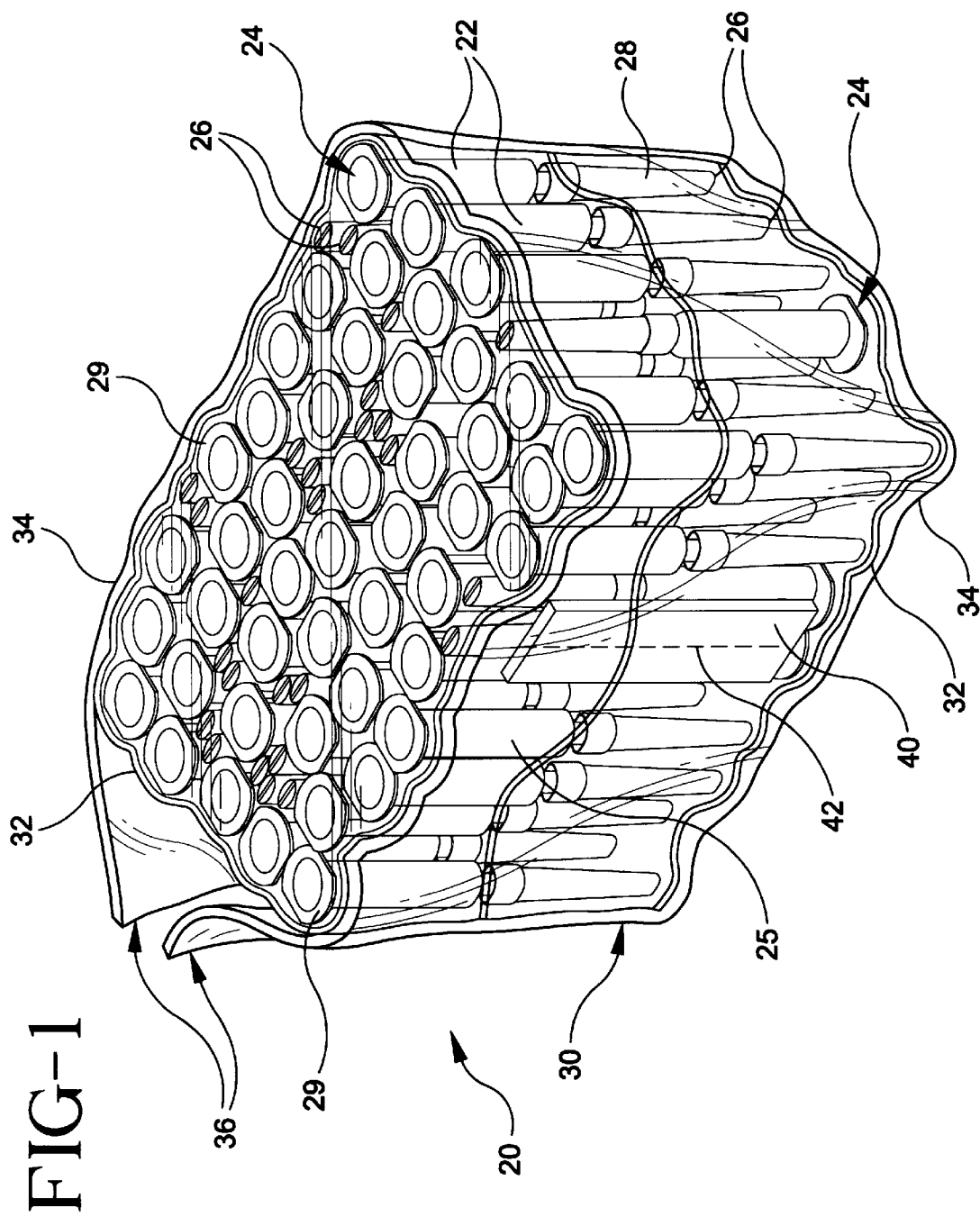
FIG. 1 is a perspective, diagrammatic illustration of an assembly of syringes designed according to this invention.

FIGS. 1 and 2 illustrate an assembly 20 of syringes 22. Each syringe 22 has a first end 24 at one end of a generally cylindrical barrel portion 25 that is adapted to contain a medicament. Each syringe 22 includes a second end 26 opposite from the first end 24. The second end 26 is, in the illustrated embodiment, a terminal end on a needle shield 28. Of course, a variety of syringe sizes and configurations can be accommodated by this invention.

Since the first ends 24 include flanges 29 that facilitate administering an injection to a patient in a conventional manner, the first ends 24 have a first outside dimension. The second ends 26, have a second outside dimension that is typically much smaller than the first outside dimension.

As illustrated, the plurality of syringes preferably are aligned so that the axis of each syringe 22 is generally parallel with the axis of all of the other syringes. Some of the syringes 22 have the first ends 24 facing in one direction while a remainder of the syringes 22 have the second end 26 facing in the same direction. In other words, a first portion of the plurality of syringes 22 has the first end 24 aligned adjacent with the second end 26 of a second portion of the syringes 22. By placing some of the syringes 22 in a right-side-up orientation with others in an upside-down orientation, the density of syringes within the assembly 20 is increased. This orientation of syringes provides the advantage of increasing the density and, therefore, reducing the number of packages required for shipping a particular number of syringes. Reducing the number of packages and increasing the density of syringes reduces overall shipping costs.

The syringes 22 are enclosed in a package 30 that includes a first layer 32 and a second layer 34. The first layer 32 completely encloses the syringes and maintains them in the illustrated alignment. The first layer 32 also encloses the syringes to protect them from outside contaminants. The first layer 32 preferably is made from a generally flexible, relatively thin plastic material. In the preferred embodiment, the first layer 32 is made from a shrink wrap plastic material. The first layer 32 can be shrink wrapped around the syringes 22 or vacuum formed to enclose the syringes 22. Alternatively the first layer 22 can be a plastic that is tightly wrapped around the syringes.

The second layer 34 encloses the first layer 32 so that it completely surrounds the first layer 32, which completely surrounds the syringes 22. The second layer 34 also preferably is made from a relatively flexible, thin plastic material.

Two layers 32 and 34 preferably are provided so that the second layer 34 is exposed to dust and outside contaminants during shipping, for example. The first layer 32, however, remains clean provided that the second layer 34 is not damaged or opened. Alternatively, more than two layers may be employed.

In FIGS. 1 and 2 the second layer 34 is shown broken open at 36 so that it can be removed from the assembly 20. A protective member 40, preferably made from a relatively rigid piece of material, can be placed between the first layer 32 and the second layer 34. The protective member 40 facilitates making a cut 42, for example, in the second layer 34, which makes the second layer easier to remove. The protective member 40 protects the first layer 32 from being damaged while cutting or breaking open the second layer 34. FIG. 2 illustrates the protective member 40 adjacent the opening 36 in the second layer 34. The protective member 40 can be as large or small as desired depending on the needs of a particular situation. The protective member 40 preferably is relatively small to facilitate obtaining the maximum density of syringes within a given assembly 20.

During the assembling process, the syringes 22 preferably are aligned in an orientation as indicated in the figures. Then the first layer 32 preferably completely encloses the syringes on all sides and the top and bottom of the package 30. The first layer 32 is then closed in a sealing manner to seal off the syringes 22 from outside contaminants. The second layer 34 is then placed around the first layer 32 so that the second layer 34 completely encloses the entire package 30 in a sealing manner. The entire package 30 then preferably is sterilized so that the syringe barrels 22 are sterilized within the package 30. The first layer 32 is sterilized within the second layer 34.

Sterilizing the package 30 after the second layer 34 is applied is preferred because the first layer 32 can then be maintained sterile along with the syringes 22. During shipping to a pharmaceutical company, for example, the second layer 34 may become dirty while the first layer 32 remains clean. This enables a pharmaceutical company to handle the packages 30 in a manner that better facilitates preserving the integrity of the sterile syringes 22. The first layer 34 can be cleaned off in a semi-clean environment. The package 30 can then be taken to a more clean environment where the second layer 34 is removed, exposing the first layer 32. The essentially sterile, clean first layer 32 and the syringes 22 can then be taken to a sterile environment where the first layer 32 can then be removed exposing the syringes 22, which are then ready for use in a conventional pharmaceutical filling operation.

A package of syringes designed according to this invention provides the advantages of reducing the amount of material needed for shipping. Further, the advantage of having a greater density of syringes per package reduces overall shipping costs. Moreover, a package 30 designed according to this invention preferably provides at least two layers of plastic material surrounding the syringes that facilitates more easily handling the syringes and preserving the integrity of their sterility under a variety of conditions.

The preceding description is exemplary rather than limiting in nature. Variations and modification may become apparent that do not necessarily depart from the purview and spirit of this invention. The scope of legal protection given to this invention is to be limited only by the following claims.

We claim:

1. An assembly of syringes, comprising:
   a plurality of syringe barrels having first and second ends, each first end having a first outside dimension and each second end having a second outside dimension that is smaller than said first outside dimension;
   said barrels being aligned with generally parallel axes with a first portion of said plurality having said first ends adjacent said second ends of a second portion of said plurality of syringe barrels;
   a first layer enclosing said plurality of syringe barrels in a sealing manner to thereby protect said syringe barrels from outside contaminants and maintain said syringe barrels in said alignment;
   a second layer enclosing said first layer in a sealing manner to thereby protect said first layer from outside contaminants.

2. The assembly of claim 1, wherein said first layer comprises a relatively thin, flexible plastic material.

3. The assembly of claim 2, wherein said first layer is a shrink wrap material.

4. The assembly of claim 2, wherein said first layer is vacuum formed about said plurality of syringe barrels.

5. The assembly of claim 1, wherein said second layer comprises a relatively thin, flexible plastic material.

6. The assembly of claim 1, wherein said second layer comprises a shrink wrap material.

7. The assembly of claim 1, wherein said plurality of syringe barrels are sterilized within said first and second layers.

8. The assembly of claim 1, wherein said first and second layers are made from an identical material.

9. The assembly of claim 1, further comprising a protective piece of relatively stiff material interposed between said first and second layers to thereby protect said first layer while allowing said second layer to be cut adjacent said protective piece.

10. A method of packaging a plurality of syringe barrels, each having a first end with a first outside dimension and a second end with a second outside dimension that is smaller than the first outside dimension, comprising the steps of:
    (A) aligning the plurality of syringes such that their axes are generally parallel and such that some of the syringes have the first end aligned with the second end of a remainder of the syringes;
    (B) enclosing the plurality of syringes in a first layer of relatively thin, plastic material;
    (C) sealing the first layer to thereby protect the syringes from outside contaminants;
    (D) enclosing the first layer in a second layer of relatively thin material; and
    (E) sealing the second layer to thereby protect the first layer from outside contaminants.

11. The method of claim 10, further comprising the step of sterilizing the syringes after performing step (E).

12. The method of claim 10, further comprising placing a protective member of relatively rigid material between the first and second layers before performing step (E).

13. The method of claim 10, wherein steps (B) and (C) are performed by shrink wrapping a plastic material around the syringes to completely enclose the syringes within the first layer.

14. The method of claim 10, wherein steps (B) and (C) are performed by vacuuming forming the first layer around the syringes.

15. The method of claim 10, wherein steps (D) and (E) are performed by shrink wrapping a plastic material around the first layer.

16. The method of claim 10, wherein steps (D) and (E) are performed by vacuum forming the second layer around the first layer.

* * * * *